United States Patent [19]
Eidenschink

[11] Patent Number: 6,030,407
[45] Date of Patent: Feb. 29, 2000

[54] DEVICE AND METHOD FOR PROTECTING A STENT DELIVERY ASSEMBLY

[75] Inventor: Thomas Carl Eidenschink, Rogers, Minn.

[73] Assignee: SciMed Life Systems, Inc., Maple Grove, Minn.

[21] Appl. No.: 09/256,805

[22] Filed: Feb. 24, 1999

[51] Int. Cl.[7] .................................................. A61M 25/00
[52] U.S. Cl. ........................ 606/198; 606/194; 604/96; 623/1
[58] Field of Search ................ 606/1, 108, 194, 606/195, 198; 604/96–101

[56] References Cited

U.S. PATENT DOCUMENTS

| | | |
|---|---|---|
| 4,930,341 | 6/1990 | Euteneuer . |
| 5,015,231 | 5/1991 | Keith et al. . |
| 5,053,007 | 10/1991 | Euteneuer . |
| 5,137,512 | 8/1992 | Burns et al. . |
| 5,352,236 | 10/1994 | Jung et al. . |
| 5,417,707 | 5/1995 | Parkola . |
| 5,419,766 | 5/1995 | Chang et al. . |
| 5,425,709 | 6/1995 | Gambale . |
| 5,425,710 | 6/1995 | Khair et al. . |
| 5,569,294 | 10/1996 | Parkola . |
| 5,584,852 | 12/1996 | Parkola . |
| 5,702,410 | 12/1997 | Klunder et al. . |
| 5,746,745 | 5/1998 | Abele et al. . |
| 5,772,669 | 6/1998 | Vrba . |
| 5,800,517 | 9/1998 | Anderson et al. . |

FOREIGN PATENT DOCUMENTS

WO 98/39056  9/1998  WIPO .

*Primary Examiner*—Michael Buiz
*Assistant Examiner*—William W. Lewis
*Attorney, Agent, or Firm*—Crompton, Seager & Tufte, LLC

[57] ABSTRACT

A guided protector for a stent delivery assembly including an arbor disposed generally in the center of a sleeve. The distal end of the arbor is joined to the sleeve using a variety of joining methods including a friction fit and plastic welding. In a preferred embodiment, the inside diameter of the sleeve is larger than the outside diameter of the stent which is being protected.

20 Claims, 3 Drawing Sheets

DEVICE AND METHOD FOR PROTECTING A STENT DELIVERY ASSEMBLY

FIELD OF THE INVENTION

The present invention relates generally to the field of angioplasty. More particularly, the present invention relates to a protector for a stent delivery assembly, which includes means for guiding the protector onto the assembly.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve the use of guidewires, balloon catheters, and stents. In these procedures, the balloon catheter is advanced over the guidewire such that the balloon is positioned within a restriction in a diseased vessel. The balloon is then inflated and the restriction in the vessel is opened. To prevent subsequent closure of the vessel or restenosis, a physician may implant a stent. The stent is implanted through the use of a stent delivery system including a stent delivery catheter and a stent. It is desirable for the physician to receive the stent delivery catheter with the stent already positioned on the catheter so that it axially surrounds a distal portion of the catheter. When the stent is delivered in this manner, it is ready for immediate deployment.

The operating room where PTA and PTCA procedures take place is commonly referred to as a "Cath. Lab". It is desirable to have stents in a large range of sizes and styles immediately available to the physician. When the physician determines which device is needed, that device can be immediately unpackaged and used in a PTA or PTCA procedure. To assure ready access to the needed devices, it is common practice to store these devices in a supply closet in close proximity to the Cath. Lab. If a hospital has multiple Cath. Labs, the supply closet may be located in a central area accessible from all of the Cath. Labs. It is desirable that the packaging of a stent delivery assembly be designed to protect the stent and the stent delivery catheter during storage in this manner.

Each stent delivery kit is handled multiple times before it is used in a PTA or PTCA procedure, thus it is desirable to package the kit in a way which will prevent any damage to the stent or the stent delivery catheter during handling and shipment. To accomplish this, it is desirable to supply the stent delivery assembly with a covering over its distal portion to protect the stent and the stent delivery catheter from damage. This covering should be easily removable when the stent delivery assembly is unpackaged. This covering should not fall off inadvertently during shipping, handling and storage. For example, if the catheter is hung vertically when it is stored, gravity should not pull the covering off the stent delivery assembly. Ideally, the guided protector will protect the stent and the stent delivery catheter right up until the moment it is used in a PTA or PTCA procedure.

Because a wide variety of stents and stent delivery catheters may be present in a Cath. Lab, it is desirable to have different sizes and styles of stents readily identified. The packaging of the stent delivery assembly should include labeling which is clear, simple and readily visible. Ideally, this labeling will remain with the stent and the stent delivery catheter right up until the moment it is used in a PTA or PTCA procedure.

SUMMARY OF THE INVENTION

The present invention may be described as a guided protector for a stent delivery assembly and a method for using the guided protector. A stent delivery assembly for use with the present invention includes a stent delivery catheter and a stent. The guided protector includes an arbor and a sleeve. The inside diameter of the sleeve is preferably larger than the outside diameter of the stent to facilitate easy removal of the guided protector from the stent delivery assembly, although some frictional contact with the stent is acceptable. The distal end of the arbor is joined to the sleeve in such a way that the arbor is positioned with its longitudinal axis generally coinciding with the longitudinal axis of the sleeve.

A method for protecting a stent delivery assembly with a guided protector includes the steps of threading or sliding the arbor into a lumen in the stent delivery catheter. Once positioned in this manner, the guided protector is moved in a proximal direction so that the arbor enters further into the lumen of the stent delivery catheter. Once the guided protector is in this position, the arbor traveling inside the lumen acts to control the travel of the guided protector. This arrangement guarantees that the guided protector will be in axial alignment with the lumen of the stent delivery catheter throughout the installation process. Once the arbor is threaded or slidably received into the lumen, the guided protector is moved in a proximal direction so that the sleeve substantially covers the stent on the distal end of the stent delivery catheter. When the stent delivery assembly is needed for a PTA or PTCA procedure, the guided protector is removed from the stent delivery assembly by grasping the sleeve and pulling in a distal direction. Once again, the arbor traveling inside the lumen acts to control the guided protector so that the guided protector is in axial alignment with the lumen of the stent delivery catheter throughout the removal process. This arrangement prevents the inside diameter of the sleeve from striking or dragging to any substantial degree across the outside diameter of the stent. In a preferred embodiment, the inside diameter of the sleeve is larger than the outside diameter of the stent. This arrangement allows the guided protector to be installed and removed with very little resistance due to friction. This arrangement also provides additional protection to the stent and the stent delivery catheter because the sleeve will not contact the stent unless it is deformed substantially due to severe mishandling. Thus, in preferred embodiments, the sleeve is generally so resistant to radial collapse unless mishandled. It is, however, recognized that a collapsible sleeve could be utilized which would still protect the stent from damage by contact with unintended surfaces.

The presence of the arbor inside the lumen of the stent delivery catheter assures that the lumen will not become closed due to material creepage during storage at elevated temperatures. The presence of the arbor also guarantees that the lumen will not become pinched shut due to mishandling. Finally, the guided protector may include alphanumeric characters or colors which identify the type and size of the stent. This identification remains with the stent delivery assembly even after it is removed from its pouch or packaging. This identification remains with the stent delivery assembly up until the moment the guided protector is removed so that the stent can be deployed in a PTA or PTCA procedure.

BRIEF DESCRIPTION OF THE DRAWINGS

Other objects in the present invention and many of the attendant advantages of the present invention will be readily appreciated as the same becomes better understood by reference to the following detailed description when considered in connection with the accompanying drawings, in which like reference numerals designate like parts throughout the Figures thereon and wherein.

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention.

Examples of constructions, materials, dimensions, and manufacturing processes are provided for selected elements. All other elements employ that which is known to those of skill in the field of the invention. Those skilled in the art will recognize that many of the examples provided have suitable alternatives which may be utilized.

Figure 1:
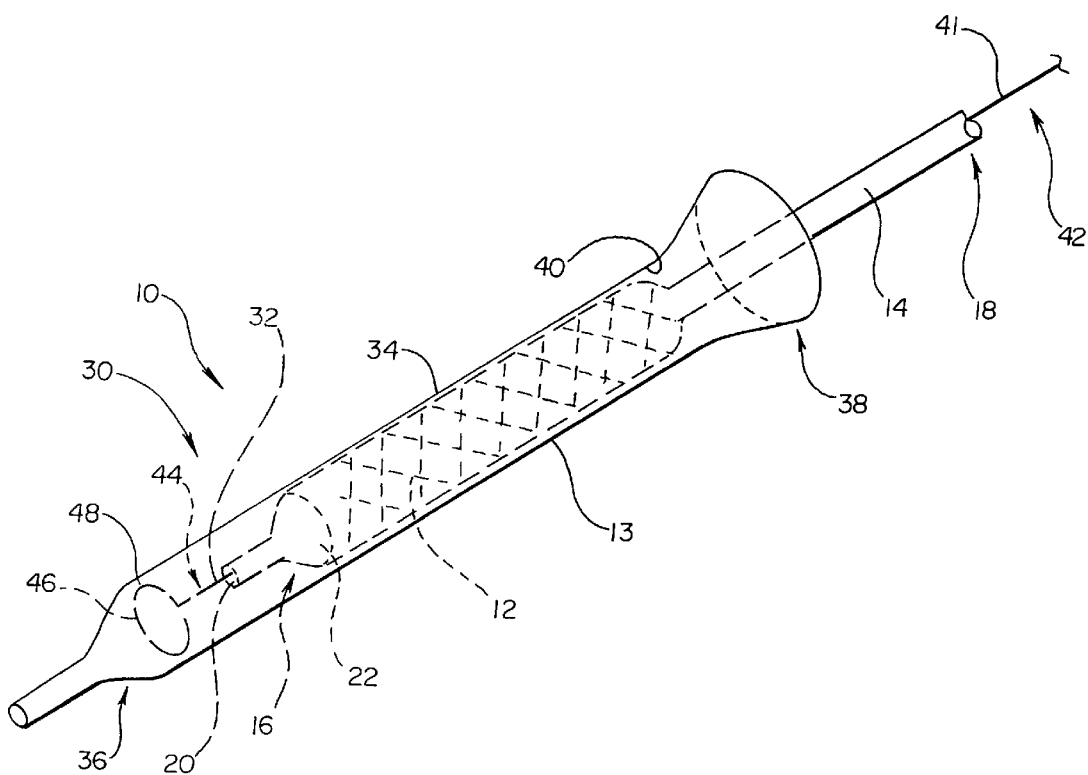
FIG. 1 is a perspective view of a preferred stent delivery assembly including a guided protector.

FIG. 1 is a perspective view of a stent delivery assembly 10, the main components of stent delivery assembly 10 are a stent delivery catheter 14 and a stent 12 with a pre-deployed outside diameter 13. Stent delivery catheter 14 includes a distal end 16, a proximal end 18, and an inner lumen 20. A generally tubular member or shaft forms the lumen. In some embodiments, stent delivery catheter 14 may also include a balloon 22. The construction and use of stents and stent delivery catheters are both well known in the art. An example of a balloon catheter suitable for use in a stent delivery application is disclosed in U.S. Pat. No. 5,746,745, the disclosure of which is incorporated herein by reference.

In FIG. 1 a guided protector 30 is seen installed on a stent delivery assembly 10. The main components of the guided protector 30 are an arbor 32 and a sleeve 34. Sleeve 34 has a distal end 36, a proximal end 38, and a lumen 40 defined by the inside diameter of the sleeve 34. The inside diameter, and thus the lumen 40 of sleeve 34 is preferably larger than outside diameter 13 of stent 12 to facilitate easy removal of guided protector 30 from stent delivery assembly 10. This arrangement also prevents damage to stent 12 and stent delivery catheter 14 if sleeve 34 is compressed slightly during handling or when it is removed.

In preferred embodiments, the sleeve 34 is a polymeric sleeve. The sleeve 34 is preferably resistant to radial collapse. This provides protection for the stent 12. It is, however, recognized that the sleeve 34 may be manufactured from a more elastic material which is readily compressed in a radial direction. The sleeve 34 would still protect the stent 12 from accident contact or abrasion with surfaces which may damage the stent 12. Further, the inside diameter of the sleeve 34 is preferably larger than the outside diameter of the stent 12 as placed on the delivery assembly 10. It is, however, recognized that the sleeve 34 may be sized to frictionally engage the exterior surface of the stent 12 during positioning and removal of guided protector 30. This is particularly true if the sleeve material is manufactured from a relatively elastic material or the sleeve is designed so that the inside diameter may be expandable. An expandable inside diameter could be achieved by designing the sleeve 34 with a longitudinal slit over its length, or spiral cutting the sleeve so that the inside diameter may be increased by rotation.

Arbor 32 is comprised of a stem 41 having a proximal end 42 and a distal end 44. In one preferred embodiment, distal end 44 of stem 41 is bent to form an eyelet 46 having an outside diameter 48. Outside diameter 48 of eyelet 46 is preferably larger than inside diameter 40 of sleeve 34. Arbor 32 is positioned in sleeve 34 with eyelet 46 in a state of compression. Due to its compressed state, eyelet 46 exerts an outward force on the inside diameter wall of sleeve 34. This outward force holds arbor 32 in position such that the longitudinal axis of arbor 32 generally coincides with the longitudinal axis of sleeve 34. This holds arbor 32 generally centered within the lumen 40 of sleeve 34. An adhesive could also be used in conjunction with the eyelet to hold the arbor 32 in place. However, this is believed unnecessary.

Figure 2:
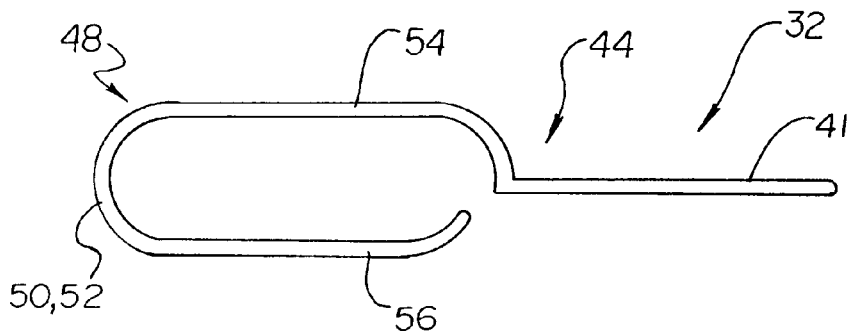
FIG. 2 is a plan view of an alternative arbor design.

FIG. 2 illustrates an alternate embodiment of arbor 32. In FIG. 2, arbor 32 includes a stem 41 having a distal end 44. Distal end 44 of stem 41 has been bent to form a sheep hook 48. Sheep hook 48 includes a curve 50 with an outer diameter 52. Sheep hook 48 also includes a first flat area 54 and a second flat area 56. Outer diameter 52 of curve 50 is preferably larger than inside diameter 40 of sleeve 34. Arbor 32 is positioned in sleeve 34 with sheep hook 48 in a state of compression. Due to its compressed state, sheep hook 48 exerts an outward force on the inside diameter wall of sleeve 34. This outward force holds arbor 32 in position such that the longitudinal axis of arbor 32 generally coincides with the longitudinal axis of sleeve 34. As with the prior embodiment, this design generally holds arbor 32 centered with the lumen 40 of sleeve 34.

Figure 3:
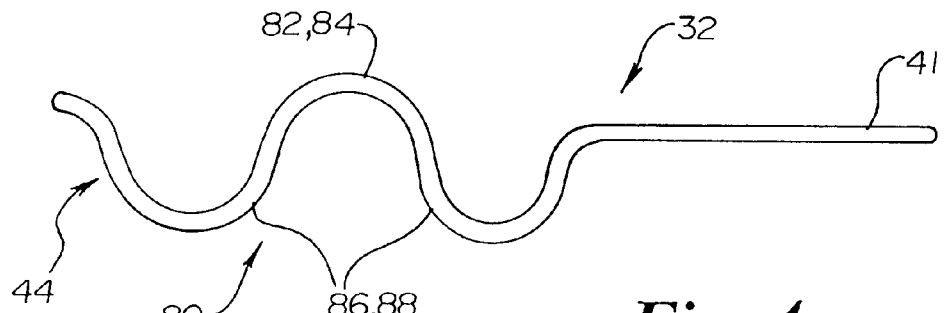
FIG. 3 is a plan view of an alternative arbor design.

FIG. 3 illustrates an alternate embodiment of arbor 32. In FIG. 3 arbor 32 includes a stem 41 having a distal end 44. Distal end 44 of stem 41 has been bent to form a wave pattern 80. Wave pattern 80 includes one or more upper curves 82 each with an outer surface 84 and one or more lower curves 86 each with an outer surface 88. The distance between outer surface 84 of upper curve 82 and outer surface 88 of the lower curve 86 is greater than the inside diameter 40 of sleeve 34.

In this embodiment, arbor 32 is positioned in sleeve 34 with wave pattern 80 in a state of compression. Due to its compressed state, wave pattern 80 exerts an outward force on the inside diameter wall of sleeve 34. This outward force holds arbor 32 in position such that the longitudinal axis of arbor 32 generally coincides with the longitudinal axis of sleeve 34. Again, arbor 32 is held generally centered within lumen 40 of sleeve 34.

Figure 4:
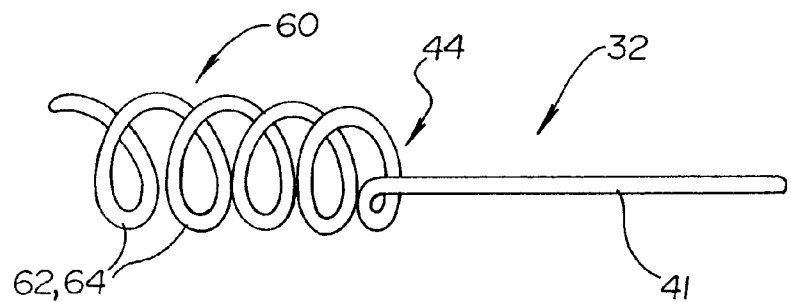
FIG. 4 is a plan view of an alternative arbor design.

FIG. 4 illustrates an alternate embodiment of arbor 32. In FIG. 4, arbor 32 includes a stem 41 having a distal end 44. Distal end 44 of stem 41 has been bent to form a coil 60 including a plurality of turns 62. Turns 62 include an outer diameter 64 which is preferably larger than inside diameter 40 of sleeve 34.

Arbor 32 is positioned in sleeve 34 with coil 60 in a state of compression. Due to its compressed state, coil 60 exerts an outward force on the inside diameter wall of sleeve 34. This outward force holds arbor 32 in position such that the longitudinal axis of arbor 32 generally coincides with the longitudinal axis of sleeve 34. Arbor 32 is generally centered within lumen 40 of sleeve 34.

Figure 5:
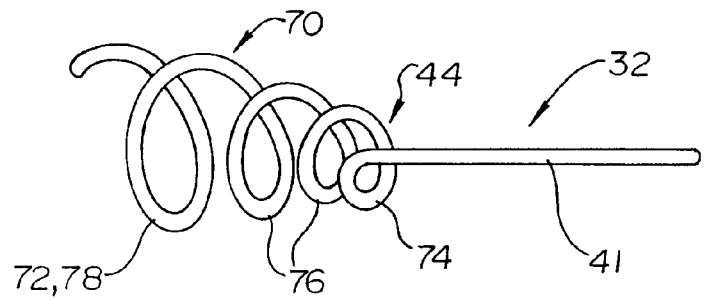
FIG. 5 is a plan view of an alternative arbor design.

FIG. 5 illustrates an alternate embodiment of arbor 32. In FIG. 5, arbor 32 includes a stem 41 having a distal end 44. Distal end 44 of stem 41 has been bent to form a conical coil 70 including a large turn 72, a small turn 74, and a plurality of intermediate turns 76. At least large turn 72 includes an outer diameter 78 which is larger than the inside diameter 40 of sleeve 34.

Arbor 32 is positioned in sleeve 34 with conical coil 70 in a state of compression. Due to its compressed state, conical coil 70 exerts an outward force on the inside diameter wall of sleeve 34. This outward force holds arbor 32 in position such that the longitudinal axis of arbor 32 generally coincides with the longitudinal axis of sleeve 34. Arbor 32 is generally centered within lumen 40 of sleeve 34.

Figure 6:
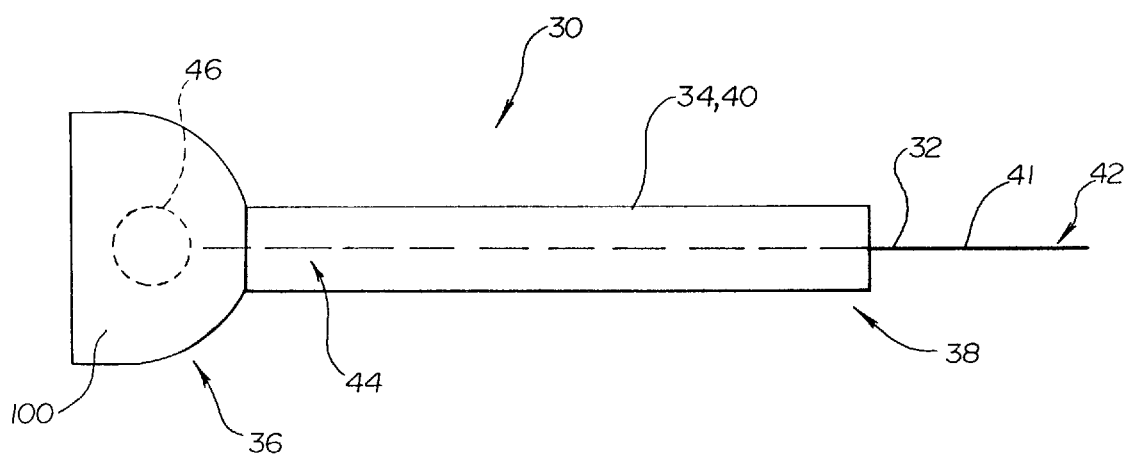
FIG. 6 is a plan view of an alternative guided protector.

FIG. 6 illustrates an alternate embodiment of guided protector 30. The main components of guided protector 30 are an arbor 32 and a sleeve 34. Arbor 32 is comprised of a stem 41 having a proximal end 42 and a distal end 44. Distal end 44 of stem 41 has been bent to form an eyelet 46. Sleeve 34 has a distal end 36, a proximal end 38 and an inside diameter 40. Distal end 36 of sleeve 34 includes a flattened tab 100. Flattened tab 100 is formed using a plastic welding process to weld inside diameter 40 of sleeve 34 closed.

Various plastic welding techniques may be used to fabricate flattened tab 100. For example, suitable welding techniques include those which use electromagnetic energy to heat the material (e.g., radio frequency welding) and those which use friction to heat the material (e.g., ultrasonic welding). Finally, in a preferred embodiment, thermal welding techniques are used to fabricate flattened tab 100. In this method of welding, an electrical heating element is used to generate the heat required for welding.

The welding process begins by positioning stem 41 inside sleeve 34 so that distal end 44 of stem 41 is proximate distal end 36 of sleeve 34. Distal end 36 of sleeve 34 is then flattened in a welding fixture. The material of sleeve 34 is heated to its melting point to form a weld joint. During welding, distal end 44 of stem 41 is surrounded by molten plastic from sleeve 34. When the molten plastic solidifies, distal end 44 of stem 41 is encased in the weld joint.

A preferred method of protecting stent delivery catheter 14 and stent 12 with guided protector 30 includes the following steps. First, guided protector 30 is held in the hand by grasping flattened tab 100 or sleeve 34. Guided protector 30 is then positioned so that proximal end 42 of stem 41 of arbor 32 is in axial alignment with lumen 20 of stent delivery catheter 14. Once positioned in this manner, guided protector 30 is moved in a proximal direction so that arbor 32 enters lumen 20 of stent delivery catheter 14. As described previously, proximal end 42 of arbor 32 preferably extends beyond proximal end 38 of sleeve 34. This arrangements aids in the process of threading or sliding arbor 32 into lumen 20 since proximal end 42 of arbor 32 is easily visualized and may be laid on top of distal end 16 of stent delivery catheter 14.

Once arbor 32 is positioned in lumen 20 of stent delivery catheter 14, guided protector 30 is moved further in a proximal direction so that sleeve 34 substantially covers stent 12 and distal end 16 of stent delivery catheter 14. Arbor 32 traveling inside lumen 20 acts to control the travel of guided protector 30. This arrangement guarantees that guided protector 30 will be in axial alignment with lumen 20 of stent delivery catheter 14 throughout the installation process.

When stent delivery catheter 14 and stent 12 are needed for a PTA or PTCA procedure, guided protector 30 is removed from stent delivery assembly 10 by grasping tab 100 or sleeve 34 and pulling in a distal direction. Once again, arbor 32 traveling inside lumen 20 acts to control the travel of guided protector 30 so that guided protector 30 is in axial alignment with lumen 20 of stent delivery catheter 14 throughout the removal process. This arrangement prevents inside diameter 40 of sleeve 34 from striking or dragging across outside diameter 13 of stent 12. In a preferred embodiment, inside diameter 40 of sleeve 34 is larger than outside diameter 13 of stent 12. Clearance between inside diameter 40 of sleeve 34 and outside diameter 13 of stent 12 allows guided protector 30 to be installed and removed with very little resistance due to friction. This arrangement also provides additional protection to stent 12 and stent delivery catheter 14 because sleeve 34 will not contact stent 12 unless it is deformed substantially due to severe mishandling.

The presence of arbor 32 inside lumen 20 of stent delivery catheter 14 assures that lumen 20 will not become closed due to material creep during storage at elevated temperatures. The presence of arbor 32 also guarantees that lumen 20 will not become pinched shut due to mishandling. Arbor 32 provides these benefits as part of guided protector 30. If arbor 32 were not attached to guided protector 30, it would be a very small component which could be easily dropped from the fingers of physician. Once dropped, this small component would be difficult to find.

Sleeve 34 and/or tab 100 may include markings which will increase the visibility of guided protector 30. The markings on tab 100 and/or sleeve 34 may include alphanumeric characters or colors which identify the type and/or size of stent 12. These markings allow a physician to quickly determine the size and type of stent 12. This identification remains with stent delivery assembly 10 even after it is removed from its pouch or its packaging. This identification remains with stent delivery assembly 10 up until the moment guided protector 30 is removed so that stent 12 can be deployed.

Guided protector 30 is held in position on distal end 16 of stent delivery catheter 14 by a friction fit between arbor 32 and lumen 20. In a preferred embodiment, the outer diameter of arbor 32 is slightly smaller than the inner diameter of lumen 20. This arrangement allows guided protector 30 to be easily installed and removed. Friction between lumen 20 and arbor 32 is sufficient to hold guided protector 30 in place until it is removed so that stent 12 can be deployed. In an alternate embodiment, the outer diameter of arbor 32 may be slightly larger than the inner diameter of lumen 20. In this arrangement, an interference fit between arbor 32 and lumen 20 holds guided protector 30 firmly in position on distal end 16 of stent delivery catheter 14. Obviously, the outside diameter of arbor 32 may also be equal to the inside diameter of lumen 20.

Having thus described the preferred embodiments of the present invention, those of skill in the art will readily appreciate that yet other embodiments may be made and used within the scope of the claims hereto attached.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A guided protector for a stent delivery assembly including a stent disposed therein, said protector comprising:

a sleeve having a proximal portion, a distal portion and a lumen extending through at least a portion thereof;

an arbor having an outside diameter, a proximal portion and a distal portion, at least a portion of the arbor disposed within said lumen; and means for disposing the arbor generally in the center of the lumen of the sleeve.

2. The guided protector of claim 1, wherein the means for disposing the arbor is formed on the distal portion of said arbor.

3. The guided protector of claim 1, wherein the distal portion of the arbor forms a friction fit with an inside wall of the sleeve forming the lumen.

4. The guided protector of claim 1, wherein the stent has an outside diameter and the lumen diameter of the sleeve is larger than the outside diameter of the stent.

5. The guided protector of claim 1, wherein the stent delivery assembly has an inner lumen, wherein, in use, at least a portion of the arbor is slidably disposed therein.

6. The guided protector of claim 5, wherein the stent delivery lumen diameter is equal to or greater than the outside diameter of the arbor.

7. The guided protector of claim 1, wherein a portion of the proximal portion of the arbor extends beyond the proximal portion of the sleeve.

8. The guided protector of claim 2, wherein the distal portion of the arbor is generally formed into the slope of an eyelet.

9. The guided protector of claim 2, wherein the distal portion of the arbor is generally formed into the shape of a hook.

10. The guided protector of claim 2, wherein the distal portion of the arbor is generally formed into the shape of a coil.

11. The guided protector of claim 2, wherein the distal portion of the arbor is generally formed into the shape of a conical coil.

12. A guided protector for a stent delivery assembly including a stent, comprising:
a sleeve having a proximal portion, a distal end, and a lumen extending through at least a portion thereof; and
an arbor having a proximal portion and a distal portion, said proximal portion disposed generally in the center of the lumen of the sleeve and extending longitudinally therein and said distal portion generally encapsulated within the distal portion of the sleeve to fix the arbor therein.

13. The guided protector of claim 12, wherein the stent has an outside diameter and the sleeve lumen diameter is greater than the outside diameter of the stent.

14. The guided protector of claim 12, wherein the stent delivery assembly has an inner lumen, wherein, in use, the arbor is slidably disposed therein.

15. The guided protector of claim 12, wherein the stent delivery assembly lumen has a diameter greater than or equal to the outside diameter of the arbor.

16. The guided protector of claim 12, wherein a portion of the proximal portion of the arbor extends beyond the proximal portion of the sleeve.

17. A method for protecting a stent delivery assembly having an inner lumen and a stent comprising the steps of:
providing a guided protector, said guided protector including a sleeve having a lumen extending through at least a portion thereof and an arbor disposed within at least a portion of the lumen;
coaxially positioning the distal end of the arbor proximate the inner lumen of a stent delivery assembly;
inserting the proximal end of the arbor into the inner lumen of the stent delivery assembly; and
moving the guided protector in a proximal direction until the stent is substantially covered by the sleeve.

18. The method of claim 17, wherein the stent has an outside diameter and the inside diameter of the sleeve is larger than the outside diameter of the stent delivery assembly.

19. The method of claim 17, wherein the stent delivery assembly has an inner lumen with an inside diameter and the outside diameter of the arbor is smaller than or equal to the inside diameter of the inner lumen of the stent delivery assembly.

20. The method of claim 17, wherein the proximal end of the arbor extends beyond the proximal end of the sleeve.

* * * * *